United States Patent [19]

Bournonville et al.

[11] Patent Number: 5,227,557
[45] Date of Patent: Jul. 13, 1993

[54] PROCESS FOR THE AROMATIZATION OF HYDROCARBONS CONTAINING 2 TO 4 CARBON ATOMS PER MOLECULE

[75] Inventors: Jean-Paul Bournonville, Cergy Pontoise; Francis Raatz, Saint Avold; Bernard Juguin, deceased, late of Rueil Malmaison, all of France, by Jeannine Juguin and Sylvie Juguin, legal representatives

[73] Assignee: Institut Francais Du Petrole, Rueil-Malmaison, France

[21] Appl. No.: 753,168

[22] Filed: Aug. 30, 1991

[30] Foreign Application Priority Data

Sep. 3, 1990 [FR] France .................. 90 10946

[51] Int. Cl.$^5$ .............................. C07C 2/00
[52] U.S. Cl. ........................ 585/419; 505/418; 502/64
[58] Field of Search ........... 585/407, 415, 418, 419; 502/64

[56] References Cited

U.S. PATENT DOCUMENTS

| | | |
|---|---|---|
| 4,036,741 | 7/1977 | Pollitzer et al. . |
| 4,072,731 | 2/1978 | Rausch . |
| 4,214,980 | 7/1980 | Le Page et al. . |
| 4,497,969 | 2/1985 | Ball et al. . |
| 4,590,322 | 5/1986 | Chu . |
| 4,727,206 | 2/1988 | Clayson et al. . |
| 4,766,265 | 8/1988 | Desmond et al. . |
| 4,806,699 | 2/1989 | Smith et al. . |
| 4,808,763 | 2/1989 | Shum . |
| 4,839,320 | 6/1989 | Trowbridge et al. . |
| 4,861,740 | 8/1989 | Sachtler et al. . |
| 4,861,934 | 8/1989 | Suzuki et al. . |
| 4,886,927 | 12/1989 | Sachtler et al. . |
| 4,922,051 | 5/1990 | Nemet-Mavrodin et al. . |
| 4,923,835 | 5/1990 | Travers et al. . |
| 5,010,048 | 4/1991 | Petit et al. . |
| 5,026,921 | 6/1991 | Degnan, Jr. et al. . |
| 5,073,673 | 12/1991 | Hirabayashi et al. . |

FOREIGN PATENT DOCUMENTS

| | | |
|---|---|---|
| 754019 | 1/1971 | Belgium . |
| 361424 | 4/1990 | European Pat. Off. . |
| 7242254 | 10/1972 | Japan . |
| 7001852 | 8/1969 | Netherlands . |

*Primary Examiner*—Anthony McFarlane
*Attorney, Agent, or Firm*—Millen, White, Zelano & Branigan

[57] ABSTRACT

For the aromatization of hydrocarbons containing 2 to 4 carbon atoms per molecule in the presence of a specific and preferably acid catalyst, the catalyst contains an MFI zeolite in which is introduced at least one noble metal from the platinum family and at least one additional metal chosen from within the group consisting of tin, germanium, lead and indium, and the catalyst optionally contains an amorphous matrix.

15 Claims, No Drawings

PROCESS FOR THE AROMATIZATION OF HYDROCARBONS CONTAINING 2 TO 4 CARBON ATOMS PER MOLECULE

BACKGROUND OF THE INVENTION

The invention relates to the use of a specific catalyst in aromatization reactions of hydrocarbons having between 2 and 4 carbon atoms per molecule.

The catalyst incorporates an MFI structure zeolite, which contains silicon and aluminium, as well as at least one noble metal from the platinum family, to which are added at least one additional metal chosen from within the group consisting of tin, germanium, indium and lead. An amorphous matrix can be added to the catalyst with a view to the shaping thereof.

The aromatization reaction of propane and butane in the presence of a catalyst containing the ZSM5 (or MFI) zeolite and gallium was discovered and patented by British Petroleum (U.S. Pat. No. 4,175,057 and U.S. Pat. No. 4,180,689). Since this data other companies and organizations have filed patent applications concerning modifications to the solid (U.S. Pat. No. 4,795,844, European patent EP-B-0252705) and/or to changes in the charge; $C_2$-$C_{12}$ fraction (European patent EP-B-0252705), ethane and ethylene (EP-B-0050021 and U.S. Pat. No. 4,350,835). The way in which the gallium is introduced has also been covered by patents (European patents EP-B-0120018 and 0184927).

The addition of another metal to the Ga-MFI system has also been envisaged with a view to improving the selectivity for aromatics aromatics selectivity and for reducing the coke quantity on the catalyst. Thus, the impregnation of a Ga/MFI catalyst by rhenium associated with platinum or palladium makes it possible to significantly improve the aromatics production selectivity (U.S. Pat. No. 4,766,265). Other patents claim the addition of platinum and palladium to the Ga-MFI catalyst (U.S. Pat. No. 4,766,265, European patents EP-B-0215579, 0216491, 0224162, 0228267 and Japanese patents 61268634, 62081329).

The addition of platinum to the MFI zeolite makes it possible to improve the conversion of propane (T. INUI, F. OKAZUNI, Y. MAKINO, Chem. Express 1 (1), 53–56, 1985). However, the methane and ethane production selectivity is significantly increased. The addition of rhenium to the platinum further accentuates the production of methane and ethane by hydrogenolysis (S. ENGELS et coll., Catalysis Today, 3, 437–443, 1988). The addition of copper (P MERIAUDEAU et coll., Zeolites: Facts, Figures, Future, 1423–29, 1989) and chromium (E. S. SHPIRO et coll. International Symposium on Zeolites as catalysts, Sorbents and Detergent builders, Wurzburg (GFR), p 73, 1988) reduces the production of methane, but the aromatics selectivity remains inferior to Ga/MFI systems. Moreover, the addition of sulphur to a Pt.MFI catalyst makes it possible to significantly improve its aromatics production selectivity on the basis of paraffins containing 6 to 12 carbon atoms (U.S. Pat. No. 4,835,336).

In French patent application 90/06 557, there is claimed a catalyst based on the associated between an MFI zeolite and a generally amorphous support or matrix, on which is deposited a noble metal from the platinum family and at least one additional metal chosen from within the group consisting of tin, germanium, indium and lead, said support also containing at least one alkali metal or alkaline earth metal chosen from within the group consisting of lithium, sodium, potassium, rubidium, cesium, barium, calcium, beryllium, magnesium and strontium. An improvement is described in the performance characteristics compared with what was known from the prior art in connection with the aromatization of light hydrocarbons.

SUMMARY OF THE INVENTION

It has now been found that the introduction of the noble metal from the platinum family (hydrogenating metal) and the additional metal directly on the MFI zeolite using procedures such as impregnation, exchange or any other known method, leads to an improvement in the catalytic performance characteristics, particularly compared with those of French patent application 90/06557.

The MFI structure zeolite of the catalyst (which is preferably acid) of the present invention can be prepared by all known methods. The synthesis of the MFI zeolite can be carried out in a conventional $OH^-$ medium, in the presence or absence of organic structuring agents and/or alcohol. The synthesis of the MFI zeolite in the $OH^-$ medium in accordance with known procedures is described in Synthesis of High Silica Zeolites, P. Jacobs and J. Martens, Studies in Surface Science and Catalysis, Vol. 33, Elsevier editor, 1987. The MFI zeolite can also be synthesized in less conventional media, such as, e.g., the fluoride medium (C.F.R. European patent EP-A-172068).

After synthesis, the MFI zeolite is transformed into a hydrogen form by the total or partial elimination of organic compounds and/or alkali metal or alkaline earth cations, which it optionally contains after synthesis. All known methods can be used for passing to the hydrogen form, such as, e.g., calcinations in an oxidizing or non-oxidizing atmosphere, ionic exchanges followed or not by calcination, various chemical treatments, etc.

All MFI zeolites synthesized in the Si-Al system are suitable for the present invention. However, their atomic ratio Si/Al is generally higher than 7, advantageously higher than 25 and preferably between 40 and 200. The hydrogenating metal is then deposited on the MFI zeolite. Any metal from group VIII of the periodic classification of elements can be suitable, but the preferred metal is platinum.

The platinum can be introduced in different ways, e.g., in the form of a tatraamine complex by cationic exchange, or in the form of hexachloroplatinic acid by impregnation.

The platinum (or optionally another noble metal from the platinum group) can consequently be incorporated into the zeolite by impregnating the latter with the aid of an adequate aqueous or nonaqueous solution containing a salt or a compound of the noble metal. The platinum is generally introduced into the zeolite in the form of chloroplatinic acid, but it is also possible to use compounds such as ammonium chloroplatinate, dicarbonyl platinum dichloride, hexahydroplatinic acid, palladium chloride and palladium nitrate.

Among the compounds of the metal or metals from the platinum group used in the present invention, reference is also made in exemplified manner to ammonium complexes.

In the case of platinum, particular reference is made to platinum IV hexaammine salts of formula $(Pt(NH_3)_6)X_4$, in which X is a halogen atom chosen from within the group formed by fluorine, chlorine, bromine and iodine and preferably X is a chlorine atom, platinum IV halopentammine salts of formula $(PtX(NH_3)_5)X_3$, platinum IV tetrahalodiammines salts of formula $Pt X_4(NH_3)_2$ in which X has the meaning given hereinbefore, complexes of platinum with halogens-polyketones and polyketone halogen compounds of formula $H(Pt(aca)_2X)$ in which X has the meaning given hereinbefore and aca represents the radical of formula $C_5H_7O_2$ derived from acetyl acetone.

The noble metal from the platinum family is preferably introduced by impregnation with the aid of an aqueous or organic solution of one of the aforementioned organometallic compounds. Among the organic solvents which can be used reference is made to paraffin, naphthene or aromatic hydrocarbons and halogen-containing organic compounds e.g. having 1 to 12 carbon atoms in their molecule. Particular reference is made to n-heptane, methyl cyclohexane, toluene and chloroform and mixtures of these solvents can also be used.

The element (or additional metal M) chosen from within the group constituted by tin, germanium, lead and indium can be introduced via compounds such as e.g. tin nitrate, bromides and chlorides, halides, lead carbonate, acetate and nitrate, germanium oxalate and chloride, indium chloride and nitrate.

The additional metal M can be introduced before or after the introduction of the noble metal. If it is introduced before the noble metal, the compound used is chosen from the group constituted by halides, nitrates, acetates, carbonates and oxalates of the additional metal. Introduction advantageously takes place in aqueous solution. In this case, before introducing the noble metal, calcining takes place in air at a temperature between 400° and 1000° C.

The additional metal M can be introduced after the introduction of the noble metal in the form of at least one organic compound chosen from the group constituted by complexes of metals M and in particular polyketone complexes, and hydrocarbyl metals, such as alkyl, cycloalkyl, aryl, alkyl aryl and aryl alkyl metals.

The introduction of the metal M advantageously takes place with the aid of a solution in an organic solvent of the organometallic compound of said metal M. It is also possible to use organohalogen compounds of the metals M. Compounds of metals M are in particular tetrabutyl tin, tetramethyl tin, tetrapropyl germanium, tetraethyl lead, indium acetyl acetonate and triphenyl indium.

The impregnation solution is chosen from within the group constituted by paraffin, naphthene or aromatic hydrocarbons containing 6 to 12 carbon atoms per molecule and halogen-containing organic compounds containing 1 to 12 carbon atoms per molecule. Reference is made to n-heptane, methyl cyclohexanane, toluene and cloroform. It is also possible to use mixtures of the solvents defined hereinbefore.

This introduction method for the metal M has already been described in U.S. Pat. 4548918. However, the combination of the platinum family metal introduction method and the metal M introduction method produces a particular synergism.

The MFI zeolite of the catalyst used in the invention contains by weight (a) approximately 0.01 to 2 and more particularly approximately 0.1 to 0.5% of at least one noble metal from the platinum family, (b) approximately 0.005 to 0.60 and preferably 0.01 to 0.50% of tin and/or 0.005 to 0.70 and preferably approximately 0.01 to 0.60 and more particularly 0.02 to 0.50% of at least one metal chosen from within the group constituted by germanium, lead and indium.

When there are at least two metals chosen from within the group constituted by tin, germanium, lead and indium, the total content of metals in said group is approximately 0.02 to 1.20, preferably 0.02 to 1.0 and more particularly 0.02 to 0.8%.

It is possible to use either a common solution of the metals which it is wished to deposit on the zeolite, or separate solutions for the metal from the platinum family and for the additional metal or metals. When several solutions are used, it is possible to carry out intermediate calcinations and/or dryings. Normally the process is completed by a calcination at e.g. between approximately 500° and 1000° C., preferably in the presence of free oxygen, e.g. by carrying out air scavenging.

Following the preparation of the catalyst, the latter is generally calcined at between 450° C. and 1000° C., but after calcination the catalyst can advantageously undergo an activation treatment under hydrogen and at high temperature, e.g. 300° to 500° C., in order to obtain a more active metallic phase. The procedure of this treatment under hydrogen e.g. consists of a slow temperature rise under a hydrogen stream until the maximum reduction temperature is e.g. between 300° and 500° C. and preferably between 350° and 450° C. and this is maintained for 1 to 6 hours.

This preparation procedure for the catalyst leads to a solid in which the metals are homogeneously distributed throughout the volume of the catalyst grain and are in a metallic state following the reduction treatment under hydrogen scavenging between 300° and 500° C. and maintaining for 1 to 6 hours under hydrogen at the final temperature chosen.

An advantageous method for the preparation of catalysts can involve the following stages:
(a) The MFI zeolite is impregnated with an aqueous solution of a compound of a metal chosen from within the group constituted by tin, germanium, indium and lead.
(b) The product obtained in stage (a) is dried.
(c) The product obtained in stage (b) is calcined.
(d) The product obtained in stage (c) is impregnated with a platinum acetyl acetonate solution in toluene.
(e) The product obtained in stage (d) is dried.
(f) The product obtained in stage (e) is calcined.
(g) The product obtained in stage (f) is reduced under a hydrogen stream.

Another advantageous method for the preparation of catalysts can involve the following stages:
(a) The MFI zeolite is impregnated with an aqueous solution of a compound of a metal chosen from within the group constituted by tin, indium, germanium and lead.
(b) The product obtained in stage (a) is dried.
(c) The product obtained in stage (b) is calcined.
(d) The product obtained in stage (c) is impregnated with an ammoniacal tetraammine platinum chloride solution.
(e) The product obtained in stage (d) is dried.
(f) The product obtained in stage (e) is calcined.
(g) The product obtained in stage (f) is reduced under a hydrogen stream.

Another advantageous method for the preparation of catalysts can be carried out with the following stages:
(a) The MFI zeolite is impregnated with an ammoniacal tetraammine platinum chloride solution.

(b) The product obtained in stage (a) is dried.
(c) The product obtained in stage (b) is calcined.
(d) The product obtained in stage (c) is reduced after a hydrogen stream.
(e) The product obtained in stage (d) is contacted with a hydrocarbon solvent and with said organic compound of metal M, e.g. by immersing the mass in a hydrocarbon solvent already containing the organic compound or by immersing the mass in a hydrocarbon solvent and then injecting into the mixture obtained a solution of the organic compound of said metal M in a hydrocarbon solvent and e.g. that in which said mass has been immersed.
(f) The product obtained in stage (e) is reduced under a hydrogen stream.

The catalyst can also contain a support or an amorphous matrix, e.g. chosen from among magnesium, aluminum, titanium, zirconium, thorium, silicon and boron oxides, considered singly or in mixtures. It is also possible to use carbon. The preferred support is alumina. The specific surface of the alumina is advantageously between 50 and 600 m²/g and preferably between 150 and 400 m²/g.

The zeolite containing the various metals described hereinbefore can be shaped with the support using any known procedure, e.g. pelletizing, extrusion, drageification, droplet coagulation, drying by atomization.

The catalyst then contains 1 to 99% by weight zeolite containing the different metals, the residue being constituted by the support or amorphous matrix.

The catalyst according to the invention can in particular be used in the aromatization of hydrocarbons containing 2 to 4 carbon atoms per molecule under the conventional operating conditions for such processes.

The following examples illustrate the invention without limiting its scope.

EXAMPLE 1

Propane is to be transformed in the presence of a MFI zeolite-based catalyst with a Si/Al atomic ratio equal to 30 containing platinum and a metal chosen from within the group constituted by tin, germanium, indium and lead.

Preparation of the MFI zeolite.

The MFI zeolite is synthesized in the presence of an organic structuring agent using one of the known formulations (U.S. Pat. No. 3,702,886). This zeolite is transformed into the H form by calcining under an air-nitrogen mixture (10% oxygen in the mixture), at 550° C. and for 4 hours, three exchanges in 5N NH$_4$NO$_3$ at 100° C. and calcining in air at 530° C. and for 5 hours under a flow rate of 5 l/h/g.

The Si/Al atomic ratio of the HMFI zeolite is equal to 30, its pore volume measured by nitrogen adsorption at 77 K exceeds 0.160 cm³/g. The metals are deposited on the MFI zeolite in accordance with the following procedures:

Catalyst A (a) The MFI zeolite is impregnated by an aqueous tin chloride solution, so that the final tin concentration of the catalyst is 0.25% by weight.
(b) The product obtained in stage (a) is dried for 1 hour at 100° to 120° C.
(c) The product obtained in stage (b) is calcined for 2 hours at 530° C.
(d) The product obtained in stage (c) is impregnated by an aqueous hexachloroplatinic acid solution so as to obtain 0.3% platinum on the final catalyst.
(e) The product obtained is dried for 1 hour at 100° to 120° C.
(f) Calcining takes place for 2 hours at 530° C.

Catalyst A: 0.3% Pt and 0.25% Sn/MFI.

Catalyst B

The MFI zeolite is impregnated according to the same procedure as for catalyst (A), except that the tin chloride is replaced by tin acetate, the remainder of the procedure being unchanged.

Catalyst B: 0.3% Pt and 0.25% Sn/MFI.

Catalyst C

The MFI zeolite is impregnated according to the same procedure as for catalyst B, except that the platinum is impregnated by means of an ammoniacal tetraamine platinum chloride solution, the rest of the procedure being unchanged.

Catalyst C: Pt 0.3% and Sn 0.25%/MFI.

Catalyst D (comparative catalyst)

The MFI zeolite is impregnated by an ammoniacal tetraamine platinum chloride solution, so as to obtain a platinum concentration of 0.3% by weight on the final catalyst.

Catalyst D: Pt 0.3%/MFI.

EXAMPLE 2

The aforementioned catalysts undergo a propane aromatization test, together with the MFI zeolite only, under the following conditions:
Temperature: 450° C.
Pressure: 0.1 Megapascal
pph: 0.5 h$^{-1}$
Charge: C$_3$H$_8$ The results are given in table 1.

TABLE 1

| Catalyst | Conversion (molar %) | Selectivity (molar %) | | | |
| --- | --- | --- | --- | --- | --- |
| | | CH$_4$ | C$_2$H$_6$ + C$_2$H$_4$ | C$_3$H$_6$ | Aromatics |
| MFI zeolite | 14 | 45 | 25 | 30 | 0 |
| Catalyst D | 40 | 40 | 30 | 10 | 20 |
| Catalyst A | 31 | 5 | 20 | 35 | 40 |
| Catalyst B | 32 | 5 | 15 | 30 | 50 |
| Catalyst C | 34 | 5 | 15 | 25 | 55 |

EXAMPLE 3

For preparing catalysts E, F and G respectively, the impregnation procedure followed is strictly identical to that used for preparing catalyst C, except that the tin acetate is replaced by germanium oxalate (catalyst E), lead nitrate (catalyst F) and indium nitrate (catalyst G), the remainder of the procedure remaining unchanged.

Catalyst E: Pt=0.3% and Ge 0.20%/MFI
Catalyst F: Pt=0.3% and Pb 0.35%/MFI
Catalyst G: Pt=0.3% and In 0.25%/MFI.

Table 2 gives the results of the propane aromatization tests carried out with these catalysts under the same conditions as defined in example 2.

TABLE 2

| Catalyst | Conversion (molar %) | Selectivity (molar %) | | | |
| --- | --- | --- | --- | --- | --- |
| | | CH$_4$ | C$_2$H$_6$ + C$_2$H$_4$ | C$_3$H$_6$ | Aromatics |
| Catalyst D | 40 | 40 | 30 | 10 | 20 |
| Catalyst C | 34 | 5 | 15 | 25 | 55 |
| Catalyst E | 32 | 5 | 17 | 26 | 52 |
| Catalyst F | 31 | 5 | 18 | 24 | 53 |
| Catalyst G | 33 | 5 | 16 | 28 | 51 |

EXAMPLE 4

The previously prepared catalyst D is reduced under a hydrogen flow for 2 hours at 450° C. 100 g of this catalyst are immersed in 300 cm³ of n-heptane. Into the n-heptane containing the catalyst are then injected 2 g of a tetra n-butyl tin solution in n-heptane (10% tin). Contact between the platinum catalyst and the tetra n-butyl tin solution is maintained for 6 hours at the heptane reflux temperature. The impregnation solution is then discharged and 3 washing operations take place with pure n-heptane at the n-heptane reflux temperature. The catalyst is then dried. It can then either undergo a calcination in air for 2 hours at 500° C., followed by a reduction under a hydrogen stream at 450° C. for 2 hours, before being filled into the reactor, or can undergo a direct reduction under a hydrogen stream at 450° C. for 2 hours before being filled into the reactor.

This gives catalyst H: Pt 0.3% and Sn 0.2%/MFI.

The results of the propane aromatization test, under conditions identical to those of example 2 are given in table 3.

TABLE 3

| Catalyst | Conversion (molar %) | Selectivity (molar %) | | | |
|---|---|---|---|---|---|
| | | $CH_4$ | $C_2H_6 + C_2H_4$ | $C_3H_6$ | Aromatics |
| Catalyst D | 40 | 40 | 30 | 10 | 20 |
| Catalyst C | 34 | 5 | 15 | 25 | 55 |
| Catalyst H | 36 | 5 | 14 | 24 | 57 |

The catalysts according to the invention (A, B, C, E, F, G and H) make it possible to obtain a good aromatics product selectivity with a limited methane selectivity.

What is claimed is:

1. A process for the aromatization of hydrocarbons containing 2 to 4 carbon atoms per molecule in the presence of at least one catalyst containing a zeolite synthesized in a system consisting essentially of silica and alumina, having the structure of an MFI zeolite and modified by metals consisting essentially of at least one noble metal from the platinum family and at least one additional metal selected from the group consisting of tin, germanium, lead and indium.

2. A process according to claim 1, wherein said zeolite contains at least one noble metal from the platinum family in a quantity of approximately 0.01 to 2% by weight and at least one additional metal chosen from the group consisting of tin, germanium, lead and indium in a quantity of approximately 0.005 to 0.60% by weight for the tin and a quantity of approximately 0.005 to 0.70% by weight for the germanium, lead or indium.

3. A process according to claim 1, wherein said zeolite contains at least one noble metal from the platinum family in a quantity of approximately 0.1 to 0.5% by weight and at least one additional metal chosen from the group consisting of tin, germanium, lead and indium in a quantity of approximately 0.01 to 0.50% by weight for the tin and in a quantity of approximately 0.01 to 0.60% by weight for the germanium, lead or indium.

4. A process according to claim 1, wherein said zeolite contains as additional metals, tin and at least one metal chosen from the group consisting of germanium, lead and indium, the total additional metal content of said zeolite being about 0.02 to 1.20% by weight.

5. A process according to claim 1, wherein said catalyst also contains a matrix.

6. A process according to claim 5, wherein said catalyst contains by weight 1 to 99% of said zeolite and 1% of said matrix.

7. A process according to claim 5, wherein said matrix is alumina.

8. A process according to claim 1, wherein the atomic ratio Si/Al is at least 25.

9. A process according to claim 1, wherein said noble metal is platinum.

10. A process according to claim 8, wherein said noble metal is platinum.

11. A process according to claim 10, wherein said zeolite contains as additional metals, tin and at least one metal chosen from the group consisting of germanium, lead, and indium, the total additional metal content of said zeolite being about 0.02 to 1.20% by weight.

12. A process according to claim 1, wherein tin is said at least one additional metal.

13. A process according to claim 3, wherein tin is said at least one additional metal.

14. A process according to claim 9, wherein tin is said at least one additional metal.

15. A process according to claim 10, wherein tin is said at least one additional metal.

* * * * *